United States Patent [19]

Baumann et al.

[11] Patent Number: 4,578,584

[45] Date of Patent: Mar. 25, 1986

[54] THERMAL WAVE MICROSCOPY USING AREAL INFRARED DETECTION

[75] Inventors: Thomas Baumann, Stuttgart, Fed. Rep. of Germany; Frank H. Dacol, White Plains; Robert L. Melcher, Mount Kisco, both of N.Y.

[73] Assignee: International Business Machines Corporation, Armonk, N.Y.

[21] Appl. No.: 573,075

[22] Filed: Jan. 23, 1984

[51] Int. Cl.[4] .............................................. G01J 1/00
[52] U.S. Cl. .................................... 250/341; 250/338
[58] Field of Search ............... 250/341, 338, 334, 330; 374/117

[56] References Cited

U.S. PATENT DOCUMENTS

| 3,790,781 | 2/1974 | Horl et al. | 250/310 |
| 4,255,971 | 3/1981 | Rosencwaig | 374/117 |
| 4,484,820 | 11/1984 | Rosencwaig | 374/117 |

FOREIGN PATENT DOCUMENTS

| 50-101869 | 8/1975 | Japan | 250/338 |
| 2112131A | 7/1983 | United Kingdom | 250/338 |

OTHER PUBLICATIONS

Wood et al., "Hemi-Ellipsoidal Mirror IR Reflect", Applied Optics, vol. 15, 4 (1976), p. 940.
Luukkola et al., "Photothermal Imaging & Thermal Waves . . . ", 1982 Ultrasonics Symposium (p. 591).

Primary Examiner—Alfred E. Smith
Assistant Examiner—Richard Hanig
Attorney, Agent, or Firm—Jackson E. Stanland

[57] ABSTRACT

A non-contact thermal imaging system based on infrared radiation detection is described which uses an energy source to provide a beam of energy that strikes a sample to be analyzed. The energy beam produces a thermal wave in the sample, there being infrared radiation emitted from the thermal wave. All of the infrared radiation emitted from the heated area of the sample is collected and directed to an infrared detector, to have a two-dimensional image of the sample. This is used to detect surface and sub-surface structure, defects, etc. The use of a focussed energy beam, such as a laser or electron beam, offers advantages. In this technique, all points of the sample are treated equally and the results are very easily interpreted to know the exact location and type of structure that is imaged in the heated area. An ellipsoidal collector is preferably used to image the emitted infrared radiation onto the detector, where the sample is located at one focal point of the ellipse, and the detector is located at the other focal point.

24 Claims, 3 Drawing Figures

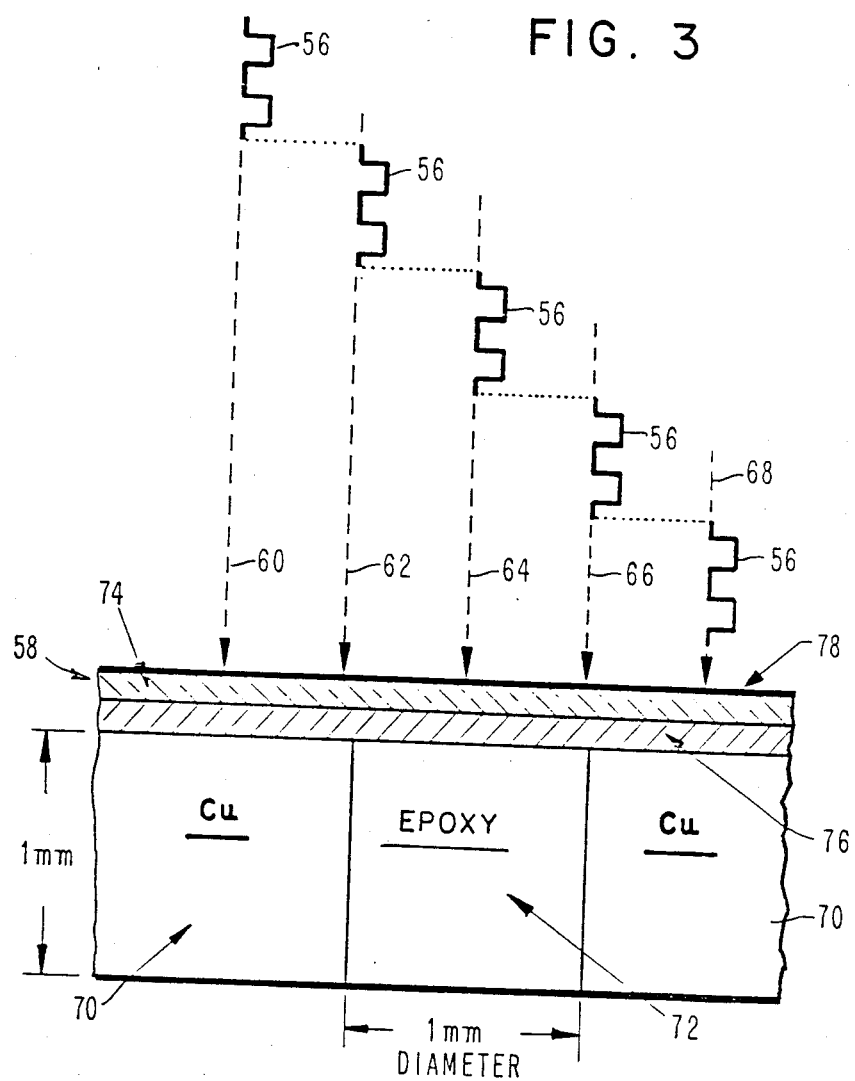

THERMAL WAVE MICROSCOPY USING AREAL INFRARED DETECTION

DESCRIPTION

1. Field of the Invention

This invention relates generally to thermal wave microscopy, and more particularly to an apparatus and method for thermal wave microscopy wherein an image from a two-dimensional area of the sample to be inspected is produced by an infrared detector that is not in contact with the sample.

2. Background Art.

In the microelectronics industry, and in other industries, there is an ever increasing need for instruments that can inspect and characterize devices and structures at various stages during their processing and manufacture. In particular, there is a need for nondestructive detection of both surface and subsurface features, particularly in devices which are essentially multilayer structures. Also, there is an increasing need for nondestructive detection and characterization of doped and modified regions in materials, such as semiconductors. One technique which is increasingly important as a nondestructive testing tool is thermal wave microscopy, which is described in more detail in the following references:

1. A. Rosencwaig, "Solid State Technology," page 91, March 1982.
2. R. L. Thomas et al, "Thermal Wave Imaging for Nondestructive Evaluation," page 586, 1982 Ultrasonic Symposium Proceedings (published by IEEE).
3. R. L. Melcher et al, IBM Technical Disclosure Bulletin, Vol. 25, No. 5, p. 2633, October 1982.

As noted in these references, thermal wave microscopy has many applications in semiconductors and in other industries using various materials. This nondestructive inspection tool can be used to image subsurface defects and to detect and characterize dopant regions. It can also be used for the measurement of the thickness of any type of thin film and to characterize oxide quality. It also can be used as an aid in pattern and mask registration and for detecting defects such as delaminations in layered structures.

In thermal wave microscopy, the properties of thermal waves in materials are utilized for nondestructive subsurface imaging. Typically, a laser or an electron beam is focussed and scanned across the surface of a sample to be analyzed. The beam is intensity-modulated at some frequency. As the beam scans across the sample, it is absorbed by the sample at or near the surface, and the periodic surface heating occurs at the modulation frequency. This periodic surface heating is the source of thermal waves that propagate from the region of incidence of the beam, i.e., from the heated region. The thermal waves interact with thermal boundaries and barriers in a manner that is mathematically similar to scattering and reflection of conventional propagating waves. Thus, any features on or beneath the surface of the sample that have thermal characteristics different from their surroundings will reflect and scatter thermal waves. In this manner, these features will become visible to the thermal waves. However, thermal waves are critically damped and travel only about one thermal wavelength, which limits the imaging range. Primarily for this reason, the beam is scanned across the sample, in order to inspect the entire sample.

Because the thermal waves are so highly damped, they are difficult to detect. However, a fraction of the thermal wave energy is always transmitted to an acoustic wave at the same frequency, because of the local stress-strain set up by the thermal waves. Thus, 1 MHz thermal waves will always give rise to 1 MHz acoustic waves. The acoustic waves are propagating waves with much longer propagation lengths than the associated thermal waves. The acoustic waves travel through condensed materials easily and are readily detected with a suitable acoustic transducer placed in acoustic contact with the sample. The acoustic detector can be in direct contact with the sample or can be coupled to it by an acoustic medium, such as gas in a gas cell surrounding the sample, or a liquid. The magnitude and phase of the acoustic waves are directly related to the interactions undergone by the thermal waves. The magnitude and phase are then measured with suitable amplitude and/or phase-sensitive electronics and recorded as a function of the beam positions. These electronic techniques and the meaning of the data so obtained are well known in the art.

The resolution obtainable in thermal wave microscopy is established by both the spot size of the laser or electron beam, and by the thermal wavelength. The thermal wavelength is in turn a function of the thermal parameters of the sample, and primarily the thermal conductivity. It is also a function of the frequency at which the intensity of the laser or electron beam is modulated.

In the practice of thermal wave microscopy, many techniques have been proposed to detect the interaction between the thermal signal and the sample. These include the following:

(a) The detection of the acoustic waves which are generated thermo-elastically in the sample (E. Brandis and A. Rosencwaig, Appl. Phys. Lett. 37, 98 (1980)).

(b) The detection of the acoustic waves which are generated in a gas surrounding the sample (U.S. Pat. Nos. 3,948,345 and 4,028,932; R. L. Thomas et al, J. Appl. Phys. 51, 1152 (1980)).

(c) The measurement of the photothermal deflection of a laser beam passing by the sample near the heated portion (D. Fournier et al., *Scanned Image Microscopy*, edited by E. A. Ash, Academic Press, London, 1980, at page 347).

(d) The detection of fluorescence of a thermally sensitive film on the sample surface (P. Kolodner et al, Appl. Phys. Lett. 42, 117, (1983)).

(e) The optical detection of thermoelastic surface deformation (A. Rosencwaig et al, Appl. Phys. Lett. 43, 166 (1983)).

(f) The temperature measurement with a sensor which is in intimate thermal contact with the sample (T. Baumann et al, Appl. Phys. Lett. 43, 71, (1983)).

(g) The detection of infrared radiation emitted by the heated portion of the sample (M. Luukkala et al, 1982 Ultrasonic Symposium Proceedings, Vol. 2, IEEE Cit. No. 82 CH 1823-4, 591;

G. Busse et al, Appl. Phys. Lett. 42, 366 (1983); and G. Busse et al, Ibid. 43, 355 (1983).

Detection methods (a)–(e) utilize interactions between the heat and other types of signals (such as thermo-elastic signals) and do not necessarily lead to results which represent the pure thermal properties of the sample. Additionally, some of these detection schemes have the disadvantage of requiring contact of a sensor to the sample, or requiring acoustic coupling between the sample and the detector. This is a disadvantage which requires messy greases, glass, gases, and so on which are typically used for direct thermal or acoustic bonding. Method (f) involves the transmission of thermal energy and is therefore suitable for analysis of thermally thin samples only. Also, some of the techniques (a)–(f) are not easily adapted to incorporation into conventional electron beam systems and provide data which are not easily interpretable in terms of the pure thermal properties of the sample. If the thermal wave generation and detection take place. in vacuum, no contact with the sample will be required, and the thermal wave microscopy apparatus can be a part of the electron beam system used for other purposes. Also, some of the techniques do not allow one to monitor both surface and transmission thermal waves and therefore yield a more limited amount of information.

Method (g) detects infrared radiation emitted by the heated portion of the sample and allows non-contact detection of sub-surface structure. However, the effect of high damping of thermal waves creates more of a problem, since it limits the location of the focus of the detector with respect to the location of the beam spot area. Also, not all illuminated spots are treated equally in that method, and a strong gradient may exist in the signals derived when the energy beam is moved to different spots on the sample. These gradients will depend on the location of the detector focus with respect to the location of the defect in the sample. Also, the amount of heat collected is not optimized by that technique which means that signal/noise is more limited. Still further, for the detection of surface particles on the sample, method (g) requires both that the beam must strike the surface particle and that the detector must be focused on the location of the beam spot. Another disadvantage with this technique is that both the beam and the detector must be scanned in order to eliminate ambiguities and detect all sub-surface defects. The data obtained using method (g) is not as easily interpretable as would be desired, although an image of the inspected sample can be obtained.

Accordingly, it is a primary object of the present invention to provide an improved technique for thermal wave microscopy which will enable the detection of surface, on the surface, and sub-surface structure and defects in a non-contact manner.

It is another object of the present invention to provide a non-destructive technique for detection of surface, on the surface, and sub-surface defects in materials using thermal wave microscopy, where an infrared detector is used which does not require contact to the sample.

It is another object of the present invention to provide improved thermal wave microscopy which provides large signals, and less noise, through efficient collection of emitted infrared radiation.

It is another object of this invention to provide a method and apparatus for thermal wave microscopy which uses infrared detection of radiation from the sample and which provides good resolution of detection of surface, on the surface, and sub-surface defects.

It is another object of this invention to provide a technique for thermal wave microscopy in which a large signal is obtained It is another object of this invention to provide an improved thermal wave microscopy technique in which particles on the sample surface can be detected without requiring both that the input beam strike the particle and that the detector be focused on the beam spot.

It is another object of the present invention to provide a technique for improved thermal wave microscopy in which all points of the sample are treated equally, and in which a two-dimensional image can be created that is easily interpreted.

It is another object of this invention to provide improved thermal wave microscopy techniques and apparatus which is easily adapted to conventional scanning electron beam systems.

DISCLOSURE OF INVENTION

In this invention, the thermal wave is generated on the surface of a sample as, for example, by directing an energy source to the surface of the sample. A suitable energy source is one that can be scanned and modulated, such as an electron beam or laser beam. This produces a thermal wave which radiates out from the point of incidence of the beam. As the thermal wave interacts with the surface, on the surface, and subsurface structure of the sample, a temperature pattern is produced on the surface in the vicinity of the heated point. This temperature pattern depends on the internal structure of the sample. The thermal response of the heated sample area leads to infrared radiation from the surface of the sample and is used to provide an image of at least the two-dimensional heated area, i.e., the hot spot created by the incidence of the beam and that portion around the hot spot which experiences the thermal wave. Means are provided for imaging this two-dimensional area to an infrared detector.

In a preferred embodiment, the entire sample area is imaged onto an infrared detector using a reflective collector which collects the emitted infrared radiation from the entire sample and directs it to the infrared detector. In this embodiment, the sample is at one focal point of an ellipsoidal reflector and the detector is at the other focal point. The entire sample surface will be imaged onto the active area of the infrared detector, as long as the sample is comparable in size to the detector. As an alternative embodiment, an areal infrared detector can be used.

In contrast with the prior techniques for thermal wave microscopy, a large area of the sample is imaged directly at each instant of time onto the infrared detector. In one preferred embodiment, the entire surface area of the sample is imaged at each instant of time onto the infrared detector. This approach treats each spot of the scanned sample equally, to provide a two-dimensional image which is easily interpreted.

Typically, the energy beam hits a single sample point for a few modulation periods. Assuming thermal steady state, the infrared signal is measured and then the beam is moved stepwise to the next point of the sample. This is continued until the entire sample surface is adequately scanned to test the entire sample for surface, on the surface, and sub-surface defects. In this technique, the detector does not have to be moved; only the incident energy source (laser or electron beam, etc.) is moved.

Another advantage is that this technique and apparatus are easily adaptable to conventional scanning electron microscopes. The electron beam of these microscopes can be used as the heat source, and the only adaptation required to perform thermal wave microscopy is the inclusion of the collector and the infrared detector. Either reflected or transmitted infrared radiation can be imaged in this technique.

These and other objects, features, and advantages will be apparent from the following more particular description of the preferred embodiments.

BRIEF DESCRIPTION OF THE DRAWINGS

FIG. 3 is a schematic illustration of an experiment which verified the success of the present invention in the detection of very small sub-surface structure.

BEST MODE FOR CARRYING OUT THE INVENTION

In the practice of this invention, thermal wave microscopy is accomplished in a manner which treats every point on the sample equally, and which collects the energy emitted from the wavefronts of each thermal wave. In contrast with the prior art in non-contact detection of thermal waves, the present invention does not collect the infrared energy from only the thermal wave which is in a direct line from the focussed energy beam source to the detector, but instead collects the infrared energy emitted across the entire two-dimensional heated area of the sample. In a preferred embodiment, the infrared energy emitted across the entire sample surface is collected, although it should be understood that the primary sources of infrared energy to the detector are the heated spot where the energy beam strikes the sample, and the portion of the sample in which the thermal waves exist. Because of very heavy damping of the thermal waves in the sample, most of the infrared energy collected by the detector will be from the spot of the sample which is struck by the energy beam and the area very close to that spot.

Figure 1:
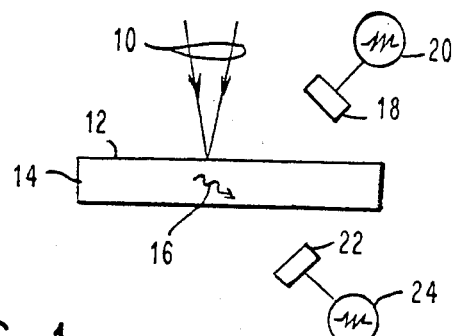
FIG. 1 schematically illustrates the technique of the present invention, where a two-dimensional area of the sample, including at least the heated area of the sample, is imaged onto an infrared detector, where either the reflected or transmitted infrared energy can be collected by the detector.

FIG. 1 schematically illustrates the principle of the present invention. In this technique, an energy beam 10 is directed to the surface 12 of sample 14. In a preferred embodiment, energy beam 10 is focussed, modulated in intensity, and scanned across the surface 12. Beam 10 is absorbed by the sample 14, producing a thermal wave 16 (i.e., a hot spot). This hot spot radiates heat to the infrared detector 18 which is connected to a display 20. If the sample is transparent to the thermal wave 16, i.e. thermally thin, the infrared radiation can be detected by an infrared detector 22, which is located on the opposite side of the sample and which is connected to another display 24.

The energy beam 10 is any type of beam which will produce a hot spot in a localized area of the surface 12 of sample 14. Energy beams which are suitable include electron beams, ion beams, particle beams and laser beams. An electron beam is a particularly suitable beam since it can be provided by conventional electron beam sources, such as scanning electron microscopes (SEM). If the energy beam is an electron beam provided by a SEM, the present invention can be easily included (with only modest investment) as an internal portion of the SEM, which allows the SEM to have additional utility.

In contrast with previous thermal wave microscopes, the present invention does not require sample contact, and will provide both surface and transmission images with simpler interpretation.

The infrared detectors 18 and 22 can be any of the several types of detectors commercially available. These differ in ease of operation and sensitivity. Pyroelectric sensors of the type available from Molectron Corp. and Plessy Corp. can be easily used, as they offer the advantages of broad spectral response, low cost, and ease of operation. For maximum sensitivity, liquid helium cooled doped Ge or Si photoconductors or liquid nitrogen cooled HgCdTe detectors can be used.

In operation, a focussed, chopped energy beam serves as a heat source. Typically, this it the electron beam of a scanning electron microscope (SEM). The beam scans the sample discontinuously, heating just discrete points of the surface. As the beam heats a single point of the surface, a thermal wave 16 propagates inside the sample. As this thermal wave interacts with the sub-structure surface, and on the surface structure of the sample, a temperature pattern is produced on the surface 12 in the vicinity of the heated point. This pattern represents the superposition of the induced thermal wave and the back-scattered thermal waves. The temperature pattern depends on the internal structure of the sample. Changes of geometry as well as changes of material, both of which cause thermal inhomogeneities, lead to changes in the surface temperature patterns. These patterns are the "thermal response" of the heated sample area, and lead to infrared radiation from the surface 12. This pattern is useful for surface and sub-surface imaging. The beam 10 heats a single sample point for a few modulation periods (such as 2–10) and, assuming thermal steady state, the infrared signal is measured just before the beam moves stepwise to the next point. If the sample is thermally transparent, the transmitted thermal wave will produce infrared radiation from the bottom surface of the sample, which can be collected by detector 22.

Figure 2:
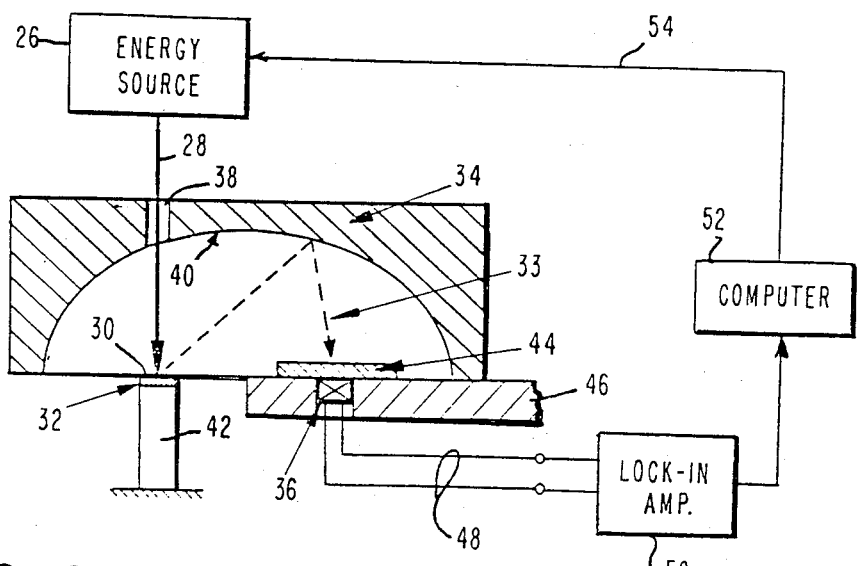
FIG. 2 shows a preferred embodiment of the present invention in which an ellipsoidal reflector is used to collect the infrared radiation emitted from the entire sample surface onto an infrared detector in order to create a two-dimensional image of the subsurface and surface structure of the sample.

FIG. 2 illustrates a preferred embodiment for the thermal wave technique of this invention. In this embodiment, an energy source 26 produces an energy beam 28 which impinges on the top surface 30 of a sample 32. In the case of an electron beam, the entire apparatus including the sample 32 is located in a vacuum chamber, as is well known in the art. The detection of the infrared radiation 33 emitted from the entire top surface 30 of the sample 32 is achieved using an infrared ellipsoidal reflector 34, where the sample 32 is located at one focal point of the ellipsoidal reflector and the infrared detector 36 is located at the other focal point. Reflector 34 has an opening 38 through which the energy beam passes to be incident onto the sample 32. The reflector 34 is chosen to be a good reflector of infrared radiation at the wavelength (e.g. 10 $\mu$m) which is predominant in the range of emitted infrared radiation. The entire reflector 34, including its ellipsoidally shaped reflecting surface 40, can be made of a highly reflective metal, such as Al.

Another alternative is to fabricate the reflector 34 of cast epoxy where the surface 40 is comprised of a layer of reflective metal, such as Al.

In FIG. 2, the sample 32 is located on a support pedestal 42, while the detector 36 is covered by a window 44. Window 44 is usually comprised of a material such as silicon and is used to block visible radiation and stray electrons from coming into contact with the detector 36. Other suitable materials for window 44 include Ge, and CdTe. The use of this window may not be necessary, but does provide more optimum operating conditions. A metal support layer 46 is provided for the detector 36, the detector by being connected via leads 48 to electronic readout circuits. In this embodiment, these circuits include the lock-in amplifier 50 and a data processing or computer system 52. Feedback line 54 is used to ensure that the sampling of the output of the detector 36 is at the same frequency as the frequency of modulation of the beam 28. As is well known in the art, amplitude and phase information can be sent from the detector 36 to a preamplifier (not shown) and then into a phase sensitive lock-in amplifier that is tuned to the modulation frequency of the energy source 26. The signal, with both phase and amplitude information, from the lock-in amplifier is then fed into a suitable storage, processing, and display system 52. System 52 also controls the rastering system or the beam deflecting system used to discontinuously scan beam 28 across the sample 32.

The ellipsoidal reflector 34 acts as a collector of infrared radiation 33 from at least the heated portion of sample 32, and usually from the entire top surface 30 of the sample. Reflector 34 has no influence on the resolution of the thermal image, and will image the entire sample surface onto the active area of the infrared detector 36 as long as the sample is comparable in size to the detector. In an example to be later described, a sample of 2 mm diameter was imaged onto a detector of approximately the same size.

The infrared signal which is detected at any instant of time originates from that portion of the sample which is heated by the beam at the same time. Only the heated part of the surface gives a significant contribution to the measured infrared signal. The resolution of the thermal image is determined by the thermal pattern on the sample surface 30 and the complete image is obtained by scanning the sample surface with the beam 28. While scanning is undertaken, the infrared signal corresponding to each point on the sample heated by the beam 28 is recorded.

The mode of operation of the thermal wave imaging system of FIG. 2 is analyzed in the following manner: the energy beam 28 is chopped with a frequency $\omega_0 = 2\pi f_0$.

The time-dependent power P(t) of a square wave modulated beam 28 is, in complex notation:

$$P(t) = P_0 + \frac{4}{\pi} P_0 \cdot \sum_{n=1,3,5,\ldots}^{\infty} \frac{1}{n} \exp(jn\omega_0 t) \quad (1)$$

with $P_0$ as a DC-power term. The beam is assumed to heat a single surface point with the coordinates, $x_p$, $y_p$. The time-dependent temperature distribution in the vicinity of this point $x_p$, $y_p$ is $$T(t,x_p,y_p,x,y,z) = T_0 + \Delta T(x_p,y_p,x,y,z) + \quad (2)$$

$$\sum_{n=1,3,5,\ldots}^{\infty} T_n(x_p,y_p,x,y,z) \exp(jn\omega_0 t).$$

$T_0$ represents the ambient room temperature. $\Delta T$ is a DC-temperature distribution caused by the DC-power and $P_0$, and $T_n$ are the amplitudes of the odd harmonic frequency components of temperature. A linear relationship between the beam power and the temperature distribution has been assumed.

However, because of the inherent nonlinearity of the Stefan-Boltzman law for black body radiation, complex notation cannot be used to evaluate the intensity, I(t, $x_p$, $y_p$), of the infrared radiation (IR) emitted by the sample when heated at ($x_p$, $y_p$):

$$I(t,x_p,y_p) = \sigma \int_{-\infty}^{+\infty} \int \epsilon[Re\{T(t,x_p,y_p,x,y,z = 0)\}]^4 dx\, dy \quad (3)$$

with $\sigma$ the Stefan-Boltzmann constant and $\epsilon = \epsilon(x,y)$ is the emissivity of the sample surface. In one example, the imaging system used a phase-sensitive narrow-band receiving system which measured only the $\omega_0$ frequency component, $I_l$, of the IR signal. $I_l$ can be calculated with a linearized approximation of eqn. (3):

$$I_1(x_p,y_p) \approx 4\sigma T_0^3 \int_{-\infty}^{+\infty} \int \epsilon[T_0 + 3\Delta T(x_p,y_p,x,y,z) = 0)] \times \quad (4)$$

$$T_1(x_p,y_p,x,y,z = 0)dx\, dy$$

On scanning the beam 28 to different sample points $x_p$, $y_p$, an image data matrix $I_l(x_p, y_p)$ is obtained. The measured data are the in-phase and quadrature values of the IR signal (related to the $\omega_0$-component of the beam power signal in eqn. (1)). Both the amplitude and the phase can be computed and used for displaying a thermal image. Under certain circumstances the phase image has some advantages. Image errors due to spatial inhomogeneities in the surface emissivity or absorption or due to the IR collection optics are all cancelled out in the phase image.

FIG. 3 schematically illustrates an experiment designed to illustrate the sensitivity and resolution of the present invention, and is described here to further explain and quantify the embodiment of FIG. 2. This experiment was carried out by using a Cambridge Instruments Mark IIA scanning electron microscope which produced the chopped and modulated beam 56. Beam 56 was scanned across the surface of sample 58, as indicated by the dashed arrows 60, 62, 64, 66, and 68. The absorbed power of beam 56 was about 2 mm, and was focussed to approximately 1 square micrometer. A Molectron P1-72 pyroelectric detector with a 2 mm diameter active area was used to detect the IR radiation. This detector, which is designed for low frequency operation, has a voltage responsivity of 200 V/W at f=15 Hz at the same frequency with 1 Hz bandwidth. A lock-in amplifier with an in-phase channel and a quadrature channel was used as a narrow-band receiver. An IBM Personal Computer was used to modulate and scan the electron beam, for data acquisition, for digital image processing, and for display.

The sample 58 consisted of a 1 mm thick copper plate 70 perforated by a cylindrical hole with 1 mm diameter filled with epoxy 72. The top surface of plate 70 was covered by a 15 μm thick glass layer 74 glued onto the copper plate 70 by an Eastman 910 glue layer 76. The thickness of layer 76 was approximately 15 μm. The entire sample surface was covered by an evaporated 500 angstroms thick nickel film 78.

The presence of the copper plate serves as a heat sink and keeps cool the portions of the layers above it which are struck by the electron beam 56. However, when beam 56 is directed to an area of the sample above the epoxy 72 (i.e., where the beam is directed along the path indicated by dashed arrow 64), a localized hot spot will be created because the copper is absent beneath this area of the sample. This hot spot creates a thermal wave which is to be detected by the pyroelectric detector. The epoxy-filled circular hole in the covered copper plate 70 was not optically visible and also was not visible in a conventional SEM-image. However, the thermal inhomogeneity of the copper plate 70 did cause variations of amplitude and phase shifts of the thermal signals and therefore was present in the infrared image. Both the thermal amplitude image of the sample of FIG. 3 and the thermal phase image of this sample clearly showed the hidden subsurface structure (hole 72 in the copper).

The thermal diffusion length of the 15 $\mu$m thick glass layer 74 is about 130 $\mu$m at f=15 Hz. The images consisted of 90×90 pixels covering a sample area of approximately 2 mm×2 mm. The image information was displayed using 16 gray levels. In the thermal amplitude image, the lowest amplitude level (black-copper present) was 90 $\mu$V, and the highest amplitude level (white-epoxy present) was 540 $\mu$V. In the thermal phase image, the background black level (in those areas where copper was present) was equivalent to a phase shift of 109 degrees, while the white level (indicative of the epoxy 72) was 145 degrees.

This experiment successfully demonstrated a non-contact thermal imaging system based on infrared radiation which was useful in imaging hidden sub-surface structures. The thermal images represent pure thermal properties of the object, there being no influence due to interactions betwen heat and other types of signals, such as acoustic waves or light.

While a modulated beam is most useful to provide improved signal/noise and resolution, it is within the practice of this invention to use dc illumination. Further, the nature of the energy source can be varied and the types of sample which can be investigated include any types of sample in which a thermal wave can be created.

In the practice of this invention, the radiation emitted from all the wavefronts of the thermal waves in the sample are collected and imaged onto a detector, in order to provide an image of the entire two-dimensional heated area. Further, if the detector area and the sample area are approximately the same, it is posssible to image the entire sample onto the detector.

This treats every point on the sample equally and leads to an imaging system whose results are readily interpretable concerning the surface and sub-surface structure of the sample.

This invention can be used to detect particles on a sample surface, such as dust particles on a semiconductor or magnetic material. In this case, the energy beam must strike the surface particle. The detector need not be focussed on the dust particle, since it will collect all of the emitted infrared information. When there is a surface particle to be detected, most of the emitted infrared radiation will come from the particle itself because of the nonlinearity of the Stefan-Boltzman law, the collector causing the emitted infrared radiation to be imaged onto the IR detector. Surface particle detection has been successfully demonstrated using the embodiment shown in FIG. 2.

Another application for the present invention is the detection of poor solder welds. For example, if a pin is soldered properly in a socket, the pin will carry away heat when a laser beam is incident on it. However, if the solder joint is bad, a hot spot will be created which will be detectable in the thermal wave pattern using, for example, the apparatus of FIG. 2.

Although it will be apparent to those skilled in the art that variations can be made to different aspects of the present invention, those variations will be within the scope of the present invention and the guidelines stated herein for the practice of this invention.

Having thus described our invention, what we claim as new, and desire to secure by Letters Patent is:

1. A non-contact method for detection of surface, on the surface, and sub-surface structure in a sample, comprising the steps of:
    irradiating a selected area of said sample with radiation in order to create a thermal wave therein which interacts with the structure of said sample to produce a temperature pattern on the surface of said sample in the vicinity of said selected area,
    imaging substantially all of the infrared radiation emitted from said sample onto a two-dimensional infrared detector having an area comparable in size to the area of said sample and being out of physical contact with said sample, to create a two-dimensional infrared image, said infrared image being characteristic of the structure of said sample in the area of said sample heated by said radiation,
    changing said selected area of said sample after each said imaging step by moving only said radiation to irradiate a different area of said sample in order to scan said sample, the position of said infrared detector being fixed during said scanning.

2. The method of claim 1, where said irradiating step is effected by impinging a modulated energy beam onto said sample, said beam being modulated at a given frequency, said infrared detector detecting said infrared radiation at said frequency of modulation of said energy beam.

3. The method of claim 1, where said irradiating step is effected by directing a focussed energy beam to the surface of said sample.

4. The method of claim 1, where said imaging step includes the collection of infrared radiation from a two-dimensional area of said sample, and the direction of said collected infrared radiation to said detector.

5. The method of claim 4, where said collecting is accomplished by the use of an ellipsoidal reflector having two focal points and which reflects infrared radiation emitted from said sample to said detector, said sample being located at one focal point of said ellipsoidal reflector and said detector being located at the other focal point of said ellipsoidal reflector.

6. The method of claim 5, where said irradiating step is effected by directing an electron beam to said sample to produce said thermal wave therein.

7. The method of claim 5, where said irradiating step is effected by directing a light beam onto said sample to produce said thermal wave in said sample.

8. The method of claim 1, where said irradiating step is effected by the use of a modulated energy beam that is scanned across said sample, said detector receiving an infrared image of a two-dimensional area of said sample, said two-dimensional area including at least the entire portion of said sample which is heated by the incidence of said energy beam thereon.

9. The method of claim 8, where said two-dimensional area includes the entire area of said sample.

10. A method for detection of surface, on the surface, and sub-surface structure in a sample, comprising the steps of:

irradiating said sample with a localized energy source which is modulated to produce a heated area thereof, said energy source producing a hot spot in said sample and a thermal wave in the region of said sample surrounding said hot spot, collecting the radiation emitted from sample from at least said hot spot and said region surrounding said hot spot, directing said collected infrared radiation to an areal infrared detector out of physical contact with said sample to create a two-dimensional image of said heated area of said sample, said detector having a size which is at least as large as said hot spot and said region surrounding said hot spot, said image being representative of the surface and sub-surface structure of said heated area of said sample, and scanning said energy source to different locations of said sample to create further two-dimensional infrared images, while maintaining in fixed positions said sample and said detector, in order to detect the surface and sub-surface structure of said sample.

11. The method of claim 10, where said collecting is accomplished by the use of an ellipsoidal reflector having two focal points, where said sample is located at one focal point of said reflector and said detector is located at the other focal point of said reflector.

12. The method of claim 11, where said electron beam is amplitude-modulated at a frequency to which said detector is set for detection of said infrared radiation emitted from the heated area of said sample.

13. The method of claim 12, where said energy source beam is focussed substantially to a point on said sample.

14. The method of claim 13, where said energy source is an electron beam.

15. The method of claim 13, where said energy source is a light beam.

16. A thermal wave device, comprising:

an energy source for creating a hot spot in a sample to be analyzed, a collector for collecting substantially all of the infrared radiation emitted from said hot spot and from the area surrounding said hot spot which is heated by a thermal wave generated at said hot spot, means for directing the collected infrared radiation from said hot spot and said surrounding heated area to an infrared detector, and an areal infrared detector onto which said collected infrared radiation is incident, said infrared detector having an area at least comparable in size to the area of said hot spot and said surrounding heated area, said detector providing a two-dimensional image of the hot spot and heated area of said sample, wherein said sample and said detector are held in fixed, spaced-apart locations, and means for scanning said energy source to create a different hot spot in said sample.

17. The device of claim 16, where said collector includes an ellipsoidal reflector having two focal points, said reflector for reflecting infrared radiation emitted from said hot spot and from said heated area to said infrared detector, said sample being located at one focal point of said ellipsoidal reflector and said detector being located at the other focal point of said ellipsoidal reflector.

18. The device of claim 16, where said energy source is an electron beam that impinges on said sample to create said hot spot.

19. The device of claim 16 where said energy source is a light beam which impinges upon said sample to create said hot spot therein.

20. The device of claim 17, where said energy source is a focussed and modulated energy beam which strikes said sample to produce said hot spot therein.

21. The device of claim 20, where said collector includes means for focussing and reflecting said collected infrared radiation to said detector.

22. The device of claim 16, where said energy source is a focussed and modulated energy beam which strikes said sample to produce said hot spot therein, said energy beam being modulated at a frequency f wherein said detector detects said emitted infrared radiation at said frequency f.

23. The device of claim 16, where said energy source is an energy beam which is directed onto said sample to produce said hot spot therein, said energy beam being scannable to different points on said sample in order to scan the entire sample for creating a two-dimensional infrared image of said entire sample.

24. A method for the detection of particles on the surface of said sample, comprising the steps of:

irradiating said particle with a localized energy beam to produce a hot spot at said particle, collecting the infrared radiation emitted from a two-dimensional area of said sample including said hot spot, and directing said collected radiation to a two-dimensional infrared detector having a size at least as great as said two-dimensional area of said sample to produce a two-dimensional image of said radiation, said image being indicative of said hot spot, said sample and said detector being held at spaced-apart locations, means for scanning said energy beam to different locations on said sample, said sample and detector being fixed at said spaced-apart locations.

* * * * *